United States Patent [19]

Nath

[11] 4,009,382
[45] Feb. 22, 1977

[54] FLEXIBLE LIGHT GUIDE, PARTICULARLY FOR MEDICAL/DENTAL USE

[76] Inventor: Günther Nath, 21 Speyrer St., Munich, Germany

[22] Filed: Feb. 3, 1975

[21] Appl. No.: 546,298

[30] Foreign Application Priority Data

| Feb. 11, 1974 | Germany | 2406424 |
| May 21, 1974 | Germany | 2424620 |
| June 21, 1974 | Germany | 2429859 |
| July 11, 1974 | Germany | 2433218 |

[52] U.S. Cl. .................... 240/1 LP; 350/96 R
[51] Int. Cl.² .................................... F21V 9/02
[58] Field of Search ............... 240/1 LP; 250/227; 350/96 R; 355/1; 340/380

[56] References Cited
UNITED STATES PATENTS

| 3,719,462 | 3/1973 | Andreatch et al. | 350/96 R |
| 3,770,350 | 11/1973 | Stone et al. | 350/96 R |
| 3,814,497 | 6/1974 | Stone | 350/96 WG |

Primary Examiner—R. L. Moses
Attorney, Agent, or Firm—Flynn & Frishauf

[57] ABSTRACT

A flexible light guide of plastic tubing is filled with a liquid which does not wet the plastic material, and preferably also is hygroscopic. The plastic material of the tube is preferably Teflon, FEP, PFA or PTFE; the liquid, for example, is an inorganic solution, especially ionic solutions and alcohols, particularly water-like polyvalent alcohols, so that light rich in ultraviolet (UV) radiation will be transmitted essentially through the solution and not deteriorate the tubing, the non-wetting characteristics providing for a sharp interface between the liquid and the tubing.

17 Claims, 1 Drawing Figure

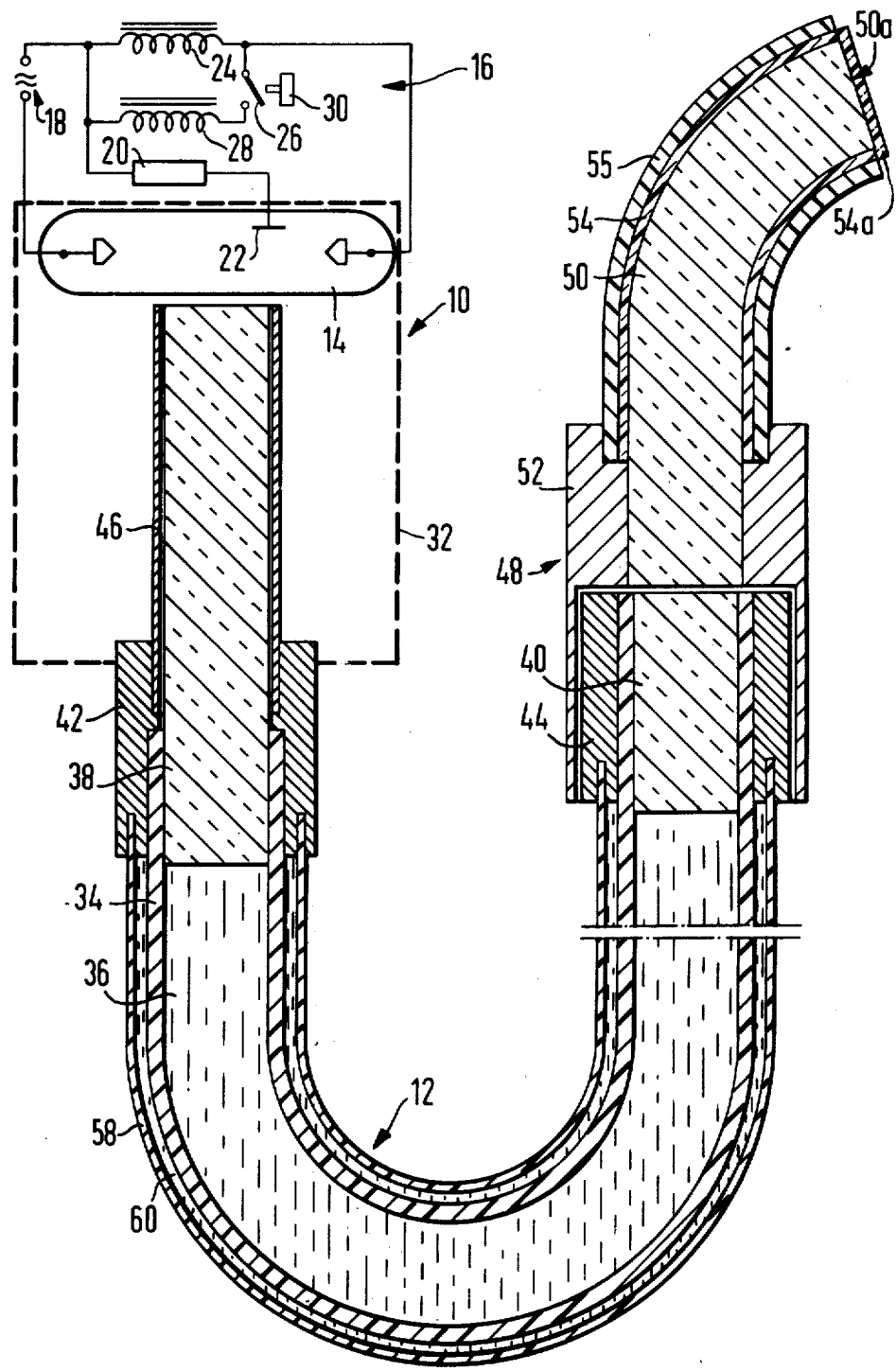

FLEXIBLE LIGHT GUIDE, PARTICULARLY FOR MEDICAL/DENTAL USE

BACKGROUND OF THE INVENTION

The present invention relates to an illuminating device formed of a flexible light guide for combination with a light source. The light guide comprises a flexible hollow tube closed at its ends and made of a plastics material, which has a predetermined index of refraction, and a light conducting liquid, which fills the flexible tube and whose refractive index is greater than that of the plastics material.

The term "light" is to be understood to mean electromagnetic radiation in the ultra-violet (UV), visible and infrared (IR) spectral ranges.

One aim of the present invention is to provide an illuminating device of the initially mentioned type which makes it possible to illuminate an object with relatively intense light and more particularly with light in the near ultra-violet and visible spectral ranges, though the invention is not to be restricted exclusively to these ranges. In particular it is an aim of the invention to provide an illuminating device which has the following advantageous properties:

a. The illuminating device is to be capable of providing an output radiative power or energy of up to several watts in continuous operation;

b. the illuminating device is to be capable of prolonged use without deteriorating, that is to say its efficiency is not to be impaired either by intensive radiation, more particularly ultra-violet radiation, nor by extended periods of operation or of storage;

c. the illuminating device is to be compact and economic in construction and should be capable of being used with light sources which are cheap to purchase and to operate, that is to say more particularly with metal vapor (for example mercury) or xenon high pressure lamps or tungsten-halogen incandescent lamps;

d. the illuminating device should be capable of being easily manipulated so that it is possible to use it even for illuminating objects which are difficult of access; and e. the light inlet angle and the transmission of the light guide of the illuminating device should be as large as possible.

An illuminating device with these properties is required for example in dentistry for polymerisation of synthetic resin fillings with ultra-violet light, for diagnostic purposes and for treatment purposes, and also for endoscopic purposes for illumination and treatment.

The previously proposed illuminating devices of the initially mentioned type all leave to be desired in one particular or another respect. Illuminating devices with fiber bundle light guides are, owing to the necessary cementing of the fiber bundle ends, not in a position to transmit high radiative powers or energies and more particularly in the ultra-violet spectral range suffer from a low efficiency.

Illuminating devices with a flexible light guide comprising a single thin quartz fiber must use an expensive laser as a light source, since such light guides cannot transmit radiation from divergent surface radiators or sources, as is the case with a high pressure mercury lamp.

Previously proposed illuminating devices with a flexible light guide, which consists of a flexible tube of plastics material and which is filled with an organic liquid, such a $CCl_4$, deteriorate with time, since the liquid diffuses out through the plastics flexible tube and/or is decomposed by ultra-violet radiation so that in the flexible tube gas bubbles or products of decomposition are produced, which reduce the transmission of the light guide and therefore the efficiency of the illuminating device to an impermissible extent. Furthermore the light transmission of such previously proposed light guides is highly temperature dependent owing to the substantial differences in the coefficients of thermal expansion of plastics and liquid.

A particular aim of the present invention is that of providing an illuminating device which has the above mentioned, advantageous properties and avoids the above mentioned disadvantages of previously proposed illuminating devices.

SUBJECT MATTER OF THE INVENTION

A flexible tube which is hollow and closed at its ends and made of a plastics material, and which has a predetermined index of refraction, includes therein a light conducting liquid, which fills the flexible tube and whose refractive index is greater than that of the plastics material.

In accordance with an aspect of the invention the liquid and the plastics material of the flexible tube are so selected that the liquid does not wet the plastics material of the flexible tube.

In accordance with another aspect of the invention the liquid is hygroscopic, that is to say it tends to take up water vapor from the surrounding atmosphere, in which the illuminating device is normally to be used.

Further features, aims and advantages of the invention will appear from the following description and the accompanying drawing.

In the single FIGURE of the drawing a preferred embodiment of the invention is shown in a somewhat simplified manner and partly as an electrical circuit diagram.

The embodiment shown in the drawing is an illuminating device for the polymerisation of plastic tooth fillings. Illuminating devices for this purpose constitute a preferred field of application of the invention, though the invention is in no way to be restricted to this field.

The illuminating device shown in the accompanying drawing comprises a light source 10 and a flexible light guide 12. The light source 10 comprises a mercury high pressure lamp 14, which is operated with a pressure in the order of magnitude of approximately 1 to 2 atmospheres gauge and, for example, has a principal electrode spacing of approximately 15 to 20 mm and a current rating of approximately 1 ampere. The principal electrodes are connected with an A.C. source 18 in series with a ballast circuit 15. The one pole of the A.C. source is connected in a conventional manner via a firing or igniting circuit 20 with a firing electrode 22.

The ballast circuit 16 comprises a first ballast choke 24, which is switched on all the time and is so dimensioned that the mercury high pressure lamp 14 has a relatively small current flowing through it, which though ensuring stable discharge, should lie as far as possible below the rating current in order to ensure the maximum length of the life of the lamp and should produce as little heat as possible, since, for example in the case of use for polymerisation in dentistry the relative duty cycle, i.e. duration of use only amounts to approximately 5 percent. The ballast choke 24 can be switched by means of a switch 26 in parallel with a second ballast choke 28, which is so dimensioned that the sum of the two ballast chokes 24 and 28 connected in parallel permits the flow of current equal to or preferably greater than the rated current. This overall current can for example amount to twice the rated current and means that the mercury high pressure lamp 14 provides a high radiative power or energy during the time in which the switch 26 is closed. The switch 26 can be closed by means of a push button 30 (which is preferably located at the light exit end of the light guide) and in practice is only operated for a short time so that the life of the lamp is not excessively reduced by overloading which takes place. The high radiative power is immediately available when the switch 26 is closed, since the lamp is kept in the warmed up condition by the low current, which flows through the ballast choke 24.

The lamp 14 is accommodated in a light-tight housing 32 which is only represented diagrammatically and the light exit end of the light guide 12 extends into this housing 32. The light guide 12 consists substantially of a flexible plastics tube 34, which is filled with a light conducting liquid 36. The ends of the plastics flexible tube are closed or sealed by cylindrical, elongated windows 38 and 40 of quartz, quartz glass or another material transparent to the radiation, in a liquid-tight manner.

A hermetic connection between the ends of the flexible tube 34 and the windows 38 and 40 respectively is brought about by cylindrical gripping members 42 and 44 respectively. The part projecting out of the gripping member 42, of the relatively long light inlet window 38 is protected by a tube 46 against mechanical damage. The tube 46 preferably consists of stainless steel and surrounds the window 38 with a small clearance. A rotatable light guide part 48 adjoins the light exit window. This part 48 which can be removed consists of a curved rod 50 transparent to radiation, which has plane ground and polished ends and at one end is held in a sleeve 52 of metals and plastics. The sleeve 52 can be fitted over the gripping member 44 and can be turned in relation to it. The diameter of the rod 50 is preferably somewhat larger than that of the window 40. The rod can for example be bent at an angle of approximately 60°. The rod 50 is covered completely or only at its front part with a tube 54 of flexible plastics material as for example Teflon FEP, which only serves for optical insulation. The flexible tube 54 of plastics is surrounded with a flexible tube 55 of silicone rubber, which protects the rod 50 against mechanical damage due to blows etc.

The light exit surface 50a of the rod 50 can be covered with a transparent layer 54a of Teflon PFA, FEP or PTFE so that the light exit surface can be pressed against body tissue can be removed again without sticking.

The window 38 consists preferably of quartz and is relatively long so that the liquid 36 is not heated by the heat produced in the light source 10. The exit window 40 and the rod 50 can consist of quartz, quartz glass or a glass with a higher refractive index as for example of the type BK 7.

The plastics flexible tube 34 consists preferably of polymer comprising carbon and halogen, more particularly fluorine, as for example polytetrafluoroethylenehexafluoropropylene ("Teflon FEP"), polytetrafluoroethylene (Teflon PTFE) or Teflon PFA ("Teflon perfluoral-koxy") or any other plastics which is sufficiently stable as regards use with the respective radiation. In the case of visible light it is possible to use for example also 4-methylpentene-1, polymethylpentene, polyvinyl chloride, polyethylene, and silicone. The preferred material for the flexible tube 34 is Teflon FEP.

The liquid 36 should in accordance with the invention not wet the inner wall of the flexible tube 34 and/or should be hygroscopic. Both these measures contribute to suppressing the outward diffusion of liquid through the flexible tube 34 to a very substantial extent so that the flexible tube 34 remains completely filled up and no gas bubbles can be formed in it, which would reduce transmission and could lead to damage of the flexible tube owing to increased radiation loading. It is important that the refractive index of the liquid 36 is somewhat higher than that of the material of the flexible tube 34, for example by up to one tenth.

Particularly suitable liquids are aqueous inorganic solutions, more particularly salt solutions as for example solutions of water-soluble alkali and alkaline earth halides, it being preferred in this case to use hygroscopic salts as for example $CaCl_2$, $CsCl$, $CsF$ and $MgCl_2$. It is also possible to use other salts as for example nitrates, phosphates and the like.

The combination of a flexible tube of plastics material, more particularly a flexible tube of Teflon FEP with an aqueous solution of an inorganic salt as a filling liquid is particularly advantageous for the following reasons: water more particularly saline water, has a high specific heat and specific heat of evaporation, so that the liquid is only slowly heated when absorbing radiation and only slowly passes into the vapor state. Furthermore Teflon FEP and water have practically the same coefficients of thermal expansion so that on heating or cooling of the light guide one need not fear either excessive pressures or the formation of gas bubbles. Since the liquid does not wet the flexible tube of plastics, the liquid does not pass into any pores present in the flexible tube of plastics either and the escape of liquid from the flexible plastics tube is substantially avoided. The absence of wetting furthermore improves the total reflection at the boundary layer between liquid and plastics material, since this boundary layer owing to the lack of wetting is relatively sharp and smooth, the latter being so because the liquid owing to the lack of wetting spans small unevennesses of the inner surface of the flexible tube of plastics and does not adapt itself to the unevennesses. In the case of use of the light guide for the transmission of UV radiation the use of an inorganic light conducting liquid as for example a concentrated aqueous $CaCl_2$ solution in contrast to the most usual organic liquids offers the advantage that the UV radiation does not bring about any decomposition or chemical changes in the liquid, something which usually leads to a reduction in transmission.

A non-wetting liquid is to be understood, as is conventional, to means a liquid, which in a vertically standing tube of the plastics material in question forms a meniscus which is upwardly convex, that is to say in the middle of the tube it lies higher than at the wall surfaces.

As liquid salt solutions it is furthermore possible to use filling liquids in the form of certain organic liquids, which do not wet the plastics material employed, as for example anhydrous or water containing alcohols and in particular polyfunctional alcohols with a suitable refractive index as for example glycerine (refractive index $n =$ approximately 1.47) or ethyleneglycol ($n =$ approximately 1.43).

The liquid can furthermore comprise coloring salts, which serve as a filter for the radiation and this feature includes more particularly the use of salts such as $CoCl_2$ and $Co(NO_3)_2$. Owing to the filtering action of the liquid it is then not necessary to use an external filter and the light source, as shown in the drawing, can be arranged directly adjacent to the light inlet end of the light guide.

In the case of a preferred embodiment the flexible tube 34 consists of Teflon FEP ($n =$ approximately 1.35) and the liquid consisted of an aqueous solution which comprised 150 g of super pure $CaCl_2.4H_2O$ per 100 ml of double distilled $H_2O$ and had a refractive index of approximately 1.43. As a dye for selective transmission in the near ultra-violet the above solution can furthermore comprise between 10 and 200 mg of $CoCl_2.6H_2O$. The addition of a small amount of $Co(NO_3)_2$ cuts out any undesired short wave UV radiation.

If the illuminating device is to be used in an environment with an extremely low water vapor pressure, the flexible tube 34 is preferably surrounded additionally with a second flexible tube 58. The flexible tube 58 shold have a minimum permeability for the liquid 36, but as regards its refractive index and other properties (smoothness of the inner wall, transparency for the radiation to be used, resistance to the radiation employed) the requirements are not so high as with respect to the flexible tube 34. Preferably the inner diameter of the flexible tube 58 is somewhat larger than the outer diameter of the flexible tube 34, so that between the two flexible tubes an intermediate space 60 remains, which is filled with the liquid 36 or any other liquid. If the liquid 36 is a solution, the liquid in the intermediate space 60 can be less concentrated or may only be made up of the solvent. The flexible tube 58 is also fixed on the gripping members 42 and 44 and consist preferably of polyethylene or silicone, which have a very low permeability for water vapor.

In practice for an illuminating device of the type described a number of different end pieces can be provided, which can be mounted instead of the end piece 48 at the light eseit end of the light guide. Such end pieces can be for example end pieces with a straight rod or a rod tapering towards the light eseit end.

Instead of a mercury high pressure lamp 14 it is possible to use another light source as for example a metal vapor or xenon high pressure lamp or super pressure lamps, or a tungsten filament incandescent lamp. The above mentioned discharge lamps can also be operated in a pulsed manner in order to increase the UV output.

The terms "water" and "aqueous solution" are also to include heavy water ($D_2O$). In the case of other filling liquids H can be completely or partly replaced by D.

What I claim is:

1. For combination with an illuminating device, a flexible light guide which comprises a flexible hollow tube of plastic material;
   light transmissive means closing the tube at its ends;
   and a light conducting liquid which has a refractive index greater than the refractive index of the plastic material of the tube and which completely fills the flexible tube between the light transmissive closing means to form a closed liquid light guide system;
   wherein the liquid filling the tube has the characteristic that the liquid does not wet the plastic material of the flexible tube; and
   wherein the liquid filling the tube has the characteristic that the liquid is hygroscopic.

2. Light guide according to claim 1, wherein the flexible tube consists of a polymer comprising carbon and fluorine.

3. Light guide according to claim 1, wherein the flexible tube consists of one of the materials Teflon FEP, Teflon PFA and polytetrafluoroethylene.

4. Light guide according to claim 1, wherein the liquid consists of an aqueous salt solution.

5. Light guide according to claim 4, wherein the liquid comprises at least one water soluble alkali metal halide or alkaline earth halide.

6. Light guide according to claim 5, wherein the liquid comprises $CaCl_2$.

7. Light guide according to claim 1, wherein the liquid comprises at least one alcohol.

8. Light guide according to claim 1, in combination with a light source, wherein the light source is an incandescent filament lamp and one end of the light guide is optically coupled with the light source.

9. Light guide according to claim 1, in combination with a light source wherein the light source is a gas discharge lamp and one end of the light guide is coupled with the light source.

10. Combination according to claim 9, wherein a ballast impedance is provided which can be switched over between a first and second impedance value, the ballast impedance being series connected to the lamp, the first impedance value being so dimensioned that a relatively low current flows through the lamp to keep the lamp warmed up, and the second impedance value being so dimensioned that a relatively high current flows through the lamp to cause the lamp to emit light.

11. Light guide according to claim 1, further comprising a second flexible tube of plastic material surrounding the flexible tube of plastics.

12. Light guide according to claim 11, further comprising a second liquid which is soluble in, or miscible with the liquid in the first plastic tube and located between the two flexible tubes of plastics.

13. Light guide according to claim 1, further comprising a removable and rotatable light guide rod located at one light outlet end of the light guide.

14. Light guide according to claim 13, wherein the light guide rod is bent.

15. Light guide according to claim 1, wherein the liquid comprises at least one heavy metal salt to provide for light filtering action.

16. Light guide according to claim 15, wherein the liquid comprises at least one of: $CoCl_2$ or $Co(NO_3)_2$.

17. Light guide according to claim 1, wherein a layer of plastic material covers at least one of the outlet surfaces of the light guide.

* * * * *